(12) United States Patent
Pazenok et al.

(10) Patent No.: US 9,096,535 B2
(45) Date of Patent: Aug. 4, 2015

(54) CF₃O-CONTAINING ENAMINOKETONES AND THEIR UTILIZATION FOR THE PREPARATION OF CF₃O-CONTAINING PYRAZOLES

(71) Applicants: BAYER INTELLECTUAL PROPERTY GMBH, Monheim (DE); CENTRE NATIONAL DE LA RECHERCHE SCIENTIFIQUE, Paris Cedex 16 (FR)

(72) Inventors: Sergii Pazenok, Solingen (DE); Bernard Langlois, Lyons (FR); Thierry Billard, Lyons (FR); Julien Barbion, Sannois (FR); Olivier Marrec, Piouigneu (FR); Jean-Pierre Vors, Saint Foy les Lyon (FR)

(73) Assignees: BAYER INTELLECTUAL PROPERTY GMBH, Monheim (DE); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/378,372

(22) PCT Filed: Feb. 13, 2013

(86) PCT No.: PCT/EP2013/052829
§ 371 (c)(1),
(2) Date: Aug. 13, 2014

(87) PCT Pub. No.: WO2013/120876
PCT Pub. Date: Aug. 22, 2013

(65) Prior Publication Data
US 2015/0018561 A1    Jan. 15, 2015

(30) Foreign Application Priority Data

Feb. 16, 2012 (EP) .................................... 12356003

(51) Int. Cl.
*C07D 231/18* (2006.01)
*C07D 405/04* (2006.01)
*C07C 221/00* (2006.01)
*C07C 225/16* (2006.01)

(52) U.S. Cl.
CPC ............ *C07D 231/18* (2013.01); *C07C 221/00* (2013.01); *C07C 225/16* (2013.01); *C07D 405/04* (2013.01)

(58) Field of Classification Search
None
See application file for complete search history.

(56) References Cited

U.S. PATENT DOCUMENTS

| 8,623,818 B2 * | 1/2014 | Greenlee et al. ............... 514/6.5 |
| 8,653,111 B2 | 2/2014 | Thede et al. |
| 2014/0031329 A1 | 1/2014 | Thede et al. |

FOREIGN PATENT DOCUMENTS

| DE | 102006050516 A1 | 4/2008 |
| DE | 102007036702 A1 | 2/2009 |
| WO | 2009141053 A1 | 11/2009 |

OTHER PUBLICATIONS

International Search Report received in corresponding PCT/EP2013/052829, mailed May 7, 2013.
Marrec et al., "A deeper insight into direcdt trifluoremethoxylation with trifluoromethyl triflate", Journal of Fluorine Chemistry, Elsevier, vol. 131, No. 2, Feb. 1, 2010, XP026871303.
Guodong et al., Highly Efficient and Clean Method for Direct Iodination of Aromatic Ketones, Synthesis, vol. 207, No. 20, Oct. 1, 2007, pp. 3113-3116, XP055031150.
Shimizu et al., "Modern Synthetic Methods for Fluorine-Substituted Target Molecules", Organofluorine Compounds, Angew. Chem. Int. Ed. 2005, 44, 214-231.
Leroux, et al., "Trifluoromethyl ethers—synthesis and properties of an unusual substituent", Beilstein Journal of Organic Chemistry 2008, 4, No. 13, 15 pages.
Sheppard, "Fluorinated Ethers. I. Aryl Fluoroalkyl Ethers", The Journal of Organic Chemistry, vol. 29, No. 1, Jan. 13, 1964, 11 pages.
Kanie, et al., "A Convenient Synthesis of Trifluoromethyl Ethers by Oxidative Desulfurization-Fluorination of Dith-iocarbonates", 2000 The Chemical Society of Japan, Bull. Chem. Soc. Jpn., 73, 471-484.
Kurobishi, et al., "Oxidative Desulfurization-Fluorination of Xanthates A Convenient Synthesis of Trifluoromethyl Ethers and Difluoro(methylthio)methyl Ethers", Tetrahedron Letters, vol. 33, No. 29, pp. 4173-4176, 1992.
Kuroboshi, et al., "Oxidative Desulfurization-Fluorination: A Facile Entry to a Wide Variety of Organofluorine Compounds Leading to Novel Liquid-Crystalline Materials", Jan. 19, 2001, Adv. Synth. Catal. 2001, 343, No. 3, Weinheim, Germany, pp. 235-250.
Rozen, "Selective Fluorinations by Reagents Containing the Of Group", Chem. Rev. 1996, 96, 1717-1736.

* cited by examiner

*Primary Examiner* — Kamal Saeed
(74) *Attorney, Agent, or Firm* — Miles and Stockbridge

(57) ABSTRACT

The present invention pertains to novel enaminoketones containing a CF₃O-group, novel pyrazole-derivatives containing a CF₃O group as well as to a novel process for their preparation comprising aminoformylation of CF₃O-ketones and cyclization of the obtained CF₃O-enaminoketones with hydrazines to trifluoromethoxy pyrazoles.

15 Claims, No Drawings

CF₃O-CONTAINING ENAMINOKETONES AND THEIR UTILIZATION FOR THE PREPARATION OF CF₃O-CONTAINING PYRAZOLES

CROSS REFERENCE TO RELATED APPLICATIONS

This application is a §371 National Stage Application of PCT/EP2013/052829, filed Feb. 13, 2013, which claims priority to EP 12356003.9, filed Feb. 16, 2012.

BACKGROUND

1. Field of the Invention

The present invention pertains to novel enaminoketones containing a CF₃O-group, novel pyrazole-derivatives containing a CF₃O group as well as to a novel process for their preparation comprising aminoformylation of CF₃O-ketones and cyclization of the obtained CF₃O-enaminoketones with hydrazines to trifluoromethoxy pyrazoles.

2. Description of Related Art

Fluorine as a substituent in active ingredients plays a significant and increasingly important role. The biggest group of fluorinated pesticides are the compounds containing a trifluoromethyl group (mainly in aromatic rings), followed by aromatic compounds containing at least one isolated fluorine atom. Only five pesticides contain OCF₃-groups are on the market. It was estimated that the number of fluorinated compounds currently under development represent some 35-50% of all the active ingredients under development as described in The pesticide manual, XIII edition; British crop protection council, 2003.

For the preparation of trifluoromethoxy substituted arenes the chlorination of aromatic methyl groups and exchange with fluorine can be used as disclosed in Yagupol'skii, L. M. Dokl. Akad. Nauk SSSR.

When aryl formates are treated with sulfur tetrafluoride, (trifluoromethoxy)arenes are obtained in yields ranging from 9-81% as described in Sheppard, W. A. J. Org. Chem. 1964, 29, 1-11.

The oxidative fluorodesulfurization fluorination allows the conversion of dithiocarbonates (xanthogenates) with a huge excess of hydrogen fluoride-pyridine and 1,3-dibromo-5,5-dimethylhydantoin into (trifluoromethoxy)arenes in moderate to excellent yields as disclosed in Kuroboshi, M.; Suzuki, K.; Hiyama, T. Tetrahedron Lett. 1992, 33, 4173-4176; Kanie, K.; Tanaka, Y.; Suzuki, K.; Kuroboshi, M.; Hiyama, T. Bull. Chem. Soc. Japan 2000, 73, 471-484; Kuroboshi, M.; Kanie, K.; Hiyama, T. Adv. Synth. Catal. 2001, 343, 235-250 and Shimizu, M.; Hiyama, T. Angew. Chem. Int. Ed. 2005, 44, 214-231.

Obviously, the best synthesis of trifluoromethyl ethers would be the direct introduction of the whole OCF₃ moiety. This was first done by radical condensation of olefins and trifluoromethyl hypofluorite (Rozen, S. Chem. Rev. 1996, 96, 1717-1736) which is highly hazardous and toxic. Then, numerous attempts to carry out nucleophilic trifluoromethoxylation with trifluoromethoxide salts failed since, generally, CF₃O— anion collapses into fluoride and fluorophosgene, even at low temperature.

DE 10 2007 036702 A1 pertains to synergistic herbicidal combinations comprising an herbicide from the group of pyrazolylphenyl derivatives optionally containing a CF₃O-group as a substituent. DE 102006 050516 A1 pertains to Dihydropyrazolon-derivatives optionally containing a CF₃O-group and processes for their synthesis for use as drugs. Both documents do not contain information about the methods of the preparation of CF₃O-derivatives nor do they disclose references indicating how such a CF₃O-group can be introduced into the pyrazol moiety or its pre-cursors.

There is presently no generally applicable procedure that allows the preparation of trifluormethoxypyrazoles. Due to the importance of heterocyclic structures in agrochemical ingredients and the use of fluorine atoms and fluorinated groups in general, the possibility to prepare OCF₃-heterocycles will lead to new, so far unknown ingredients.

There is thus a strong need for a generally applicable process for the preparation of —OCF₃ pyazoles.

SUMMARY

It was therefore an object of the present invention to provide a generally applicable and economically viable process which can be implemented on the industrial scale for preparing —OCF₃ pyazoles.

The problem has been solved according to the present invention by a process for the preparation of trifluoromethoxypyrazoles of formula V-1 or V-2 by first preparing functionalized enaminoketones of formula (I) and then transforming these functionalized enaminoketones into the trifluoromethoxypyrazoles of formula V-1 or V-2.

In one aspect, the present invention thus relates to a process for preparing an enaminoketone of formula I

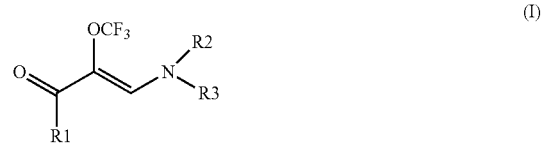

wherein
$R^1$ is $C_5$-$C_{10}$ aryl, optionally substituted by 1 to 5 halogen atoms, or $C_5$-$C_{10}$ aryl exhibiting one, two or more heteroatoms selected from oxygen and nitrogen, and
$R^2$ and $R^3$ are independently $C_1$-$C_6$ alkyl, $C_5$-$C_{10}$ aryl, $C_5$-$C_{10}$ aryl exhibiting one, two or more heteroatoms selected from oxygen and nitrogen, or form together a 5 or 7 membered ring
which comprises
(A) reacting a CF₃O-ketone of the formula II

wherein $R^1$ is as defined above
with an aminoformylation reagent.

DETAILED DESCRIPTION OF A PREFERRED EMBODIMENT

According to a preferred embodiment of the inventive process for preparing an enaminoketone of formula I,
$R^1$ in formula I or II is 2-furyl, phenyl, or phenyl substituted with one or two chlorine atoms and
$R^2$ and $R^3$ in formula I are independently $C_1$-$C_6$ alkyl.

According to an even more preferred embodiment of the inventive process for preparing an enaminoketone of formula I,
$R^1$ in formula I or II is 2-furyl, phenyl, chlorophenyl or dichlorophenyl and
$R^2$ and $R^3$ in formula I are $C_1$ alkyl.

The present invention further relates to a process for preparing trifluoromethoxypyrazoles of formula V-1 or V-2

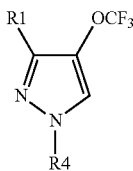 (V-1)

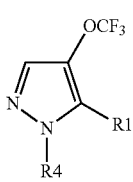 (V-2)

wherein
R¹ is as defined above
R⁴ is H, or $C_1$-$C_6$ Alkyl
which comprises
(A) reacting a $CF_3O$-ketone of the formula II

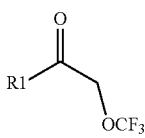 (II)

wherein R¹ is as defined above
with an aminoformylation reagent to an enaminoketone of formula I

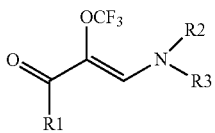 (I)

wherein
R¹, R² and R³ are as defined above
and
(B) reacting the enaminoketone of formula (I) with an hydrazine of formula IV

R⁴—NH—NH₂ (IV)

wherein R⁴ is as defined above.

The present invention further relates to a process for regioselectively preparing trifluoromethoxypyrazoles of formula V-1

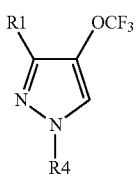 (V-1)

wherein
R¹ and R⁴ are as defined above which comprises
(A) reacting a $CF_3O$-ketone of the formula II

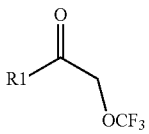 (II)

wherein
R¹ is as defined above
with an aminoformylation reagent to an enaminoketone of formula I

 (I)

wherein
R¹, R² and R³ are as defined above
and
(B) reacting the enaminoketone of formula (I) with an hydrazine of formula IV

R⁴—NH—NH₂ (IV)

wherein
R⁴ is as defined above, with the proviso that R4 is not hydrogen
wherein (B) is performed in a solvent selected from the group consisting of methanol, ethanol, and trifluoroethanol.

According to a preferred embodiment of the inventive processes for preparing trifluoromethoxypyrazoles of formula V-1 or V-2 or for regioselectively preparing trifluoromethoxypyrazoles of formula V-1, R4 in formula IV, V-1, or V-2 is H, or $C_1$-Alkyl.

Step (A) comprises reacting trifluoromethoxyketones according to formula (II) with an aminoformylation reagent according to the subsequent reaction scheme 1:

Scheme 1

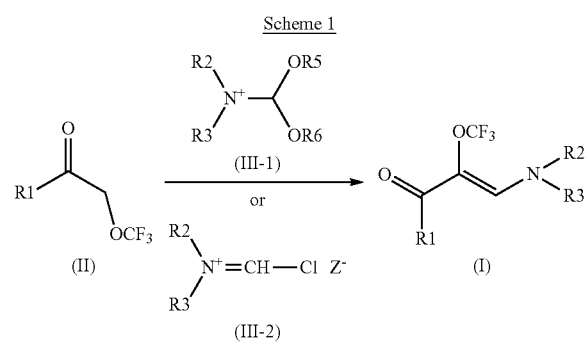

Trifluoromethoxyketones of the formula (II) are commercially available or can be prepared according to the method described in: Marrec, et al. Advanced Synthesis & Catalysis (2010), 352(16), 2831-2837, WO 2009141053 A1 20091126, DE 102008024221, Marrec, et al. Journal of Fluorine Chemistry (2010), 131(2), 200-207.

Trifluoromethoxyketones of the formula (II) can be prepared in two steps starting from the corresponding methylketones. First, methylketones are directly α-iodinated by the following literature processes (Synthesis 2007, 3113-3116; Tetrahedron Lett. 2006, 47, 6883-6886). Then, the resulting α-iodo-methylketones react with trifluoromethyltriflate, in presence of AgF, to perform the substitution of iodine by $CF_3O$ group.

Surprisingly it has been found that 2-(trifluoromethoxy) ketones smoothly react with e.g. Dimethylformamide dimethylacetal to give the novel $CF_3O$-enaminones.

For the aminoformylation, the following reagents can be used: dimethylformamide dimethylacetal, dimethylformamide diethylacetal, phenymethylformamidedimethylacetal, or $DMF/POCl_3$ (which are the precursors of compound III-2 by a Vilsmeier reaction). These reagents are commercially available. According to an especially preferred embodiment of the present invention, Dimethylformamide diethylacetal is used as aminoformylation reagent.

Thus, according to a further embodiment of the present invention, the aminoformylation reagent used for (A) is selected from a compound of the formula III-1

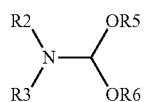

(III-1)

wherein $R^2$ and $R^3$ are as defined above and $R^5$ and $R^6$ are $C_1$-$C_6$-Alkyl and a compound of the formula III-2

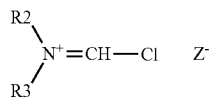

(III-2)

wherein $R^2$ and $R^3$ are as defined above.

According to a further embodiment of the present invention, (A), as described above, is performed at a temperature of from 50° C. to 150° C. More preferably, (A) is performed at a temperature of from 80° C. to 120° C.

According to a further embodiment of the present invention, (A) is performed in a solvent selected from DMF, toluene, xylenes, chlorobenzenes, and dimethylacetamide.

According to yet another embodiment of the present invention, the reaction time is 3-10 h. More preferably, the reaction time is 4-5 h.

Step (B) Cyclization

Step (B) comprises converting enaminoketones of the formula (I) into trifluoromethoxy pyrazoles of the formula (V-1 or V-2) by cyclization with hydrazines of formula (IV) according to the subsequent scheme 2

Scheme 2

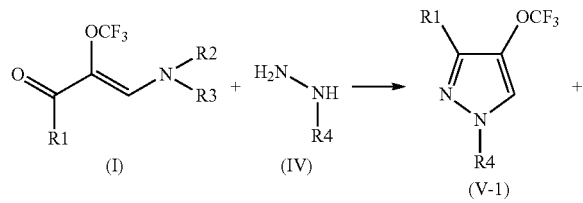

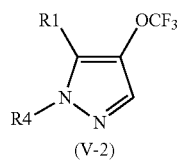

(V-2)

$R^1$, $R^2$, $R^3$, and $R^4$ are as defined above.

With methylhydrazine, the 2 regioisomeric pyrazoles in a ratio of 60:40 were obtained in acetic acid.

According to a preferred embodiment of the present invention, the process for regioselectively preparing 1-methyl-4-trifluoromethoxy-pyrazoles is performed by using a less acidic solvent, selected from methanol, ethanol, and trifluoroethanol.

According to a further embodiment of the present invention, the cyclisation (B) is performed in different solvents selected from alcohols, preferably methanol, ethanol, or isopropanol, nitriles, preferably acetonitrile, or butyronitrile, amides, preferably dimethylformamide, or dimethylacetamide, and organic acids, preferably formic acid or acetic acid. Most preferred solvents for the cyclisation (B) are methanol and ethanol.

According to a further embodiment of the present invention, the cyclization (B) is performed at a temperature ranging from 0° C. to 50° C., more preferably at a temperature ranging from 15° C. to 30° C., most preferably at room temperature.

According to a further embodiment of the present invention, pyrazoles of the formula (I) can be further transformed to novel pyrazolic acids bearing a $CF_3O$-group, if $R^1$ is 2-Furyl (scheme 3).

Scheme 3

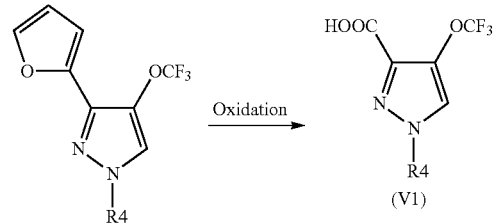

The present invention thus further relates to a process for preparing trifluoromethoxypyrazolic acids of formula VI

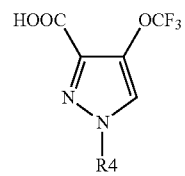

(VI)

wherein $R^4$ is as defined above, which comprises oxidizing a compound of formula V-1, wherein $R^1$ is 2-furyl and $R^4$ is as defined above.

According to a further embodiment of the present invention, the trifluoromethoxypyrazolic acids of formula VI are obtained by oxidizing the compound of formula V-1, wherein $R^1$ is 2-furyl and $R^4$ is as defined above, using an oxidant selected from $RuCl_3/NaIO_4$, $RuO_4$, $O_3$, $KMnO_4$, and $CrO_3$.

According to a further preferred embodiment of the present invention, if the system RuCl$_2$/NaIO is used, 0.05 equivalents of RuCl$_3$ and 10 equivalents of NaIO$_4$ are used for 1 equivalent of pyrazole.

The choice of the solvent for the reaction of scheme 3 is very important. It should be inert towards the oxidant. According to a further preferred embodiment of the present invention, the process for preparing trifluoromethoxypyrazolic acids of formula VI is performed in a solvent selected from hexane/AcOEt/H$_2$O, CCl$_4$/CH$_3$CN/H$_2$O, H$_2$O/MeCN/AcOEt, and H$_2$O/CH$_2$Cl$_2$/MeCN. Most preferred is the use of hexane/AcOEt/H$_2$O. Preferred ratios are 1/1/2 for a mixture of hexane/AcOEt/H$_2$O and 2/2/3 for a mixture of CCl$_4$/CH$_3$CN/H$_2$O.

The oxidation is performed at a temperature ranging from 0° C. to 50° C., more preferably at a temperature ranging from 10° C. to 30° C., most preferably at room temperature.

The present invention further relates to a compound of formula I

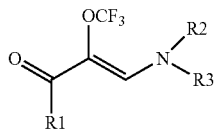

wherein
R$^1$, R$^2$ and R$^3$ are as defined above.

The present invention further relates to a compound of formula V-1 or V-2

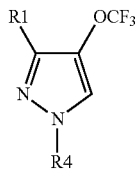

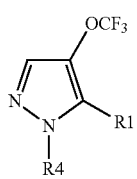

wherein R$^1$ and R$^4$ are as defined above.

The present invention further relates to a compound of formula V-1

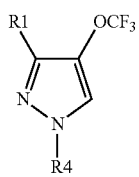

wherein R$^1$ and R$^4$ are as defined above.

The present invention further relates to a compound of formula VI

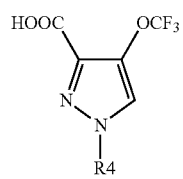

wherein
R$^4$ is as defined above.

General Definitions

In connection with the present invention, the term halogen (—X) comprises, unless otherwise defined, those elements which are chosen from the group consisting of fluorine, chlorine, bromine and iodine, fluorine, chlorine and bromine being preferably used and fluorine and chlorine being particularly preferably used.

Appropriately substituted groups can be mono- or polysubstituted, it being possible for the substituents in polysubstitutions to be identical or different.

Alkyl groups substituted with one or more halogen atoms (—X) are chosen, for example, from trifluoromethyl (CF$_3$), difluoromethyl (CHF$_2$), CF$_3$CH$_2$, ClCH$_2$, CF$_3$CCl$_2$ and CHF$_2$CCl$_2$.

Alkyl groups in connection with the present invention are, unless otherwise defined, linear, branched or cyclic hydrocarbon groups which can optionally exhibit one, two or more heteroatoms chosen from oxygen, nitrogen, phosphorus and sulphur. In addition, the alkyl groups according to the invention can optionally be substituted by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C═O)R') and amide (—CONR'2) groups, R' being hydrogen or a C$_{1-12}$-alkyl group, preferably a C$_{2-10}$-alkyl group, particularly preferably a C$_{3-8}$-alkyl group, which can exhibit one or more heteroatoms chosen from nitrogen, oxygen, phosphorus and sulphur.

The definition C$_1$-C$_{12}$-alkyl comprises the biggest range defined herein for an alkyl group. Specifically, this definition comprises, for example, the meanings methyl, ethyl, n-propyl, isopropyl, n-butyl, isobutyl, sec-butyl and t-butyl, n-pentyl, n-hexyl, 1,3-dimethylbutyl, 3,3-dimethylbutyl, n-heptyl, n-nonyl, n-decyl, n-undecyl and n-dodecyl.

The definition cyclic C$_{3-12}$-alkyl groups comprises the biggest range defined herein for a cyclic alkyl group. Specifically, this definition comprises, for example, the meanings cyclopropyl, cyclobutyl, cyclopentyl, cyclohexyl, cycloheptyl and cyclooctyl.

Alkenyl groups in connection with the present invention are, unless otherwise defined, linear, branched or cyclic hydrocarbon groups which comprise at least one single unsaturation (double bond) and can optionally exhibit one, two or more single or double unsaturations or one, two or more heteroatoms chosen from oxygen, nitrogen, phosphorous and sulphur. In addition, the alkenyl groups according to the invention can optionally be substituted by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C═O)R') and amide (—CONR'2) groups, R' being hydrogen or a C$_{1-12}$-alkyl group, preferably a C$_{2-10}$-alkyl group, particularly preferably a C$_{3-8}$-alkyl group, which can exhibit one or more heteroatoms chosen from nitrogen, oxygen, phosphorous and sulphur.

The definition $C_2$-$C_{12}$-alkenyl comprises the biggest range defined herein for an alkenyl group. Specifically, this definition comprises, for example, the meanings vinyl; allyl (2-propenyl), isopropenyl(1-methylethenyl); but-1-enyl(crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

Alkynyl groups in connection with the present invention are, unless otherwise defined, linear, branched or cyclic hydrocarbon groups which comprise at least one double unsaturation (triple bond) and can optionally exhibit one, two or more single or double unsaturations or one, two or more heteroatoms chosen from oxygen, nitrogen, phosphorous and sulphur. In addition, the alkynyl groups according to the invention can optionally be substituted by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C=O)R') and amide (—CONR'2) groups, R' being hydrogen or a linear, branched or cyclic $C_{1-12}$-alkyl group which can exhibit one or more heteroatoms chosen from nitrogen, oxygen, phosphorous and sulphur.

The definition $C_2$-$C_{12}$-alkynyl comprises the biggest range defined herein for an alkynyl group. Specifically, this definition comprises, for example, the meanings ethynyl(acetylenyl); prop-1-ynyl and prop-2-ynyl.

Aryl groups in connection with the present invention are, unless otherwise defined, aromatic hydrocarbon groups which can exhibit one, two or more heteroatoms chosen from oxygen, nitrogen, phosphorous and sulphur and can optionally be substituted by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C=O)R') and amide (—CONR2') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_{5-18}$-aryl comprises the biggest range defined herein for an aryl group having 5 to 18 atoms. Specifically, this definition comprises, for example, the meanings cyclopentadienyl, phenyl, cycloheptatrienyl, cyclooctatetraenyl, naphthyl and anthracenyl.

The definition $C_{5-18}$-aryl groups exhibiting one, two or more heteroatoms chosen from oxygen, nitrogen, phosphorous and sulphur are chosen, for example, from the group consisting of 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in connection with the present invention are, unless otherwise defined, alkyl groups substituted by aryl groups which can exhibit a C1-8-alkylene chain and can be substituted in the aryl backbone or the alkylene chain by one or more heteroatoms chosen from oxygen, nitrogen, phosphorous and sulphur and optionally by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C=O)R') and amide (—CONR2') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_{7-19}$-aralkyl group comprises the biggest range defined herein for an arylalkyl group with a total of 7 to 19 atoms in the backbone and alkylene chain. Preference is given to those $C_{7-19}$-aralkyl groups comprising 5 or 6 carbon atoms or heteroatoms in the aryl backbone and 1 to 8 carbon atoms in the alkylene chain. Specifically, this definition comprises, for example, the meanings benzyl and phenylethyl.

Alkylaryl groups (alkaryl groups) in connection with the present invention are, unless otherwise defined, aryl groups substituted by alkyl groups which can exhibit a $C_{1-8}$-alkylene chain and can be substituted in the aryl backbone or the alkylene chain by one or more heteroatoms chosen from oxygen, nitrogen, phosphorous and sulphur and optionally by additional groups chosen from —R$^{1'}$, halogen (—X), alkoxy (—OR'), thioether or mercapto (—SR'), amino (—NR'2), silyl (—SiR'3), carboxyl (—COOR'), cyano (—CN), acyl (—(C=O)R') and amide (—CONR2') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_{7-19}$-alkylaryl group comprises the biggest range defined herein for an alkylaryl group with a total of 7 to 19 atoms in the backbone and alkylene chain. Preference is given to those $C_{7-19}$-aralkyl groups comprising 5 or 6 carbon atoms or heteroatoms in the aryl backbone and 1 to 8 carbon atoms in the alkylene chain. Specifically, this definition comprises, for example, the meanings tolyl-, 2,3-, 2,4-, 2,5-, 2,6-, 3,4- or 3,5-dimethylphenyl.

The alkyl, alkenyl, alkynyl, aryl, alkylaryl and aralkyl groups can furthermore exhibit one or more heteroatoms which, unless otherwise defined, are chosen from nitrogen, oxygen, phosphorous and sulphur. The heteroatoms in this connection replace the carbon atoms indicated.

The compounds according to the invention can exist, if appropriate, as mixtures of different possible isomeric forms, in particular of stereoisomers, such as, e.g., E- and Z-isomers, threo- and erythro-isomers, and optical isomers, but, if appropriate, also tautomers. Both the E- and Z-isomers, as also the threo- and erythro-isomers, and also the optical isomers, any mixture of these isomers, and the possible tautomeric forms, are disclosed and claimed.

EXPERIMENTAL PART

Direct α-Iodination of Aromatic Ketones (Synthesis of Educts for Synthesis of Compounds of Formula II)

Finely powdered CuO (1.0 eq.) and 12 (1.0 eq.) were added to a well-stirred solution of the ketone in anhydrous MeOH (C=0.25M). The mixture was stirred for 5 min and then refluxed. After disappearance of the reactant (monitored by TLC), the mixture was filtered and the solvent was removed under reduced pressure. The residue was poured into 10% Na$_2$S$_2$O$_3$ solution (10 mL/mmol of ketone), the mixture was extracted with AcOEt (3×) and the organic layer was dried (Na$_2$SO$_4$). Removal of the solvent and purification of the residue by column chromatography gave the target products (Synthesis 2007, 3113-3116).

Ketone (1.0 eq.) along with I$_2$ (4.0 eq.) in DME (C=0.2M) was heated in a round-bottomed flask at an oil bath temperature of 90° C. for 3 h. Then the contents were cooled and extracted with AcOEt (2×). The combined extract was washed with Na$_2$S$_2$O$_3$ to remove unreacted iodine. Subsequently, the extract was washed with brine (10 mL), dried over MgSO$_4$ and concentrated. The crude product was purified by silica gel chromatography and the corresponding α-iodo product was isolated (Tetrahedron Lett. 2006, 47, 6883-6886).

2-(Iodoacetyl)furan

Brown oil (at 25° C.). 1H NMR (300 MHz, CDCl$_3$): δ=7.63 (dd, J=1.8/0.9 Hz, 1H), 7.32 (dd, J=3.6/0.9 Hz, 1H), 6.58 (dd, J=3.6/1.8 Hz, 1H), 4.24 (s, 2H). 13C NMR (75 MHz, CDCl$_3$): δ=181.9, 149.6, 146.9, 118.8, 112.8, 0.6.

1-(Iodoacetyl)-3,5-dichlorobenzene

Brown oil (at 25° C.). 1H NMR (300 MHz, CDCl$_3$): δ=7.82 (d, J=1.8 Hz, 2H), 7.55 (dd, J=1.8/1.8 Hz, 1H), 4.34 (s, 3H). 13C NMR (75 MHz, CDCl$_3$): δ=190.2, 139.1, 135.7, 135.6, 133.2, 127.2, 0.9.

1-(Iodoacetyl)-2,3-dichlorobenzene

Brown oil (at 25° C.). 1H NMR (300 MHz, CDCl$_3$): δ=7.49 (dd, J=8.1/1.5 Hz, 1H), 7.35 (dd, J=7.5/1.5 Hz, 1H), 7.22 (dd, J=8.1/7.5 Hz, 1H), 4.33 (s, 2H). 13C NMR (75 MHz, CDCl$_3$): δ=194.3, 138.1, 133.7, 132.6, 128.8, 127.7, 127.5, 6.1.

Nucleophilic Trifluoromethoxylation with TFMT and AgF (Synthesis of Compounds of Formula II)

In a 10 mL round-bottomed flask, equipped with a rubber septum and a magnetic stirrer, AgF (1.1 eq.) was introduced. Under argon atmosphere, anhydrous CH$_3$CN (C=0.5M) was added and the heterogeneous mixture was cooled to −30° C. TFMT (1.1 eq., 300 µL/mmol of iodoacetyl aromatic compound was then added, the vessel was tightly closed (autogenous pressure of COF$_2$ is needed to allow the reaction to proceed) and the reaction mixture was stirred for 2 h at −30° C. After addition of the electrophile (1.0 eq., neat when liquid or dissolved in the minimum of CH$_3$CN when oil or solid) by the mean of a gas-tight syringe, stirring was continued at −30° C. for 30 min then at r.t. for 24 h (in the dark). Finally, the vessel was depressurised and the reaction mixture was filtered over Celite®. The filtrate was concentrated in vacuo, the residue was dissolved in DCM, washed with brine, dried over MgSO$_4$, filtered and concentrated in vacuo. Purification by chromatography over silica gel finally afforded the pure corresponding trifluoromethyl ether (J. Fluorine Chem. 2010, 131, 200-207).

1-phenyl-2-(trifluoromethoxy)ethanone

Yellow oil. 1H NMR (300 MHz, CDCl$_3$): δ=7.91 (m, 2H); 7.65 (m, 1H); 7.52 (m, 2H); 5.18 (s, 2H). 13C NMR: 190.2; 134.4; 133.8; 129.1; 127.9; 121.8 (q, J=256.3); 68.4 (q, J=2.9). 19F NMR (282 MHz, CDCl$_3$): δ=−61.44 (s, CF$_3$)

1-(2-Furyl)-2-(trifluoromethoxy)ethanone

Brown oil (at 25° C.). 1H NMR (300 MHz, CDCl$_3$): δ=7.63 (dd, J=1.5/0.6 Hz, 1H), 7.35 (dd, J=3.6/0.6 Hz, 1H), 6.61 (dd, J=3.6/1.5 Hz, 1H), 5.01 (s, 2H). 13C NMR (75 MHz, CDCl$_3$): δ=179.4, 150.1, 147.2, 121.6 (q, 1JC-F=255.0), 118.8, 112.8, 67.6 (q, 3JC-F=3.0). 19F NMR (282 MHz, CDCl$_3$): δ=−61.65 (s).

1-(Trifluoromethoxyacetyl)-3,5-dichlorobenzene

Brown oil (at 25° C.). 1H NMR (300 MHz, CDCl$_3$): δ=7.74 (d, J=1.8 Hz, 2H), 7.59 (dd, J=1.8/1.8 Hz, 1H), 5.12 (s, 3H). 13C NMR (75 MHz, CDCl$_3$): δ=188.1, 136.1, 135.9, 133.9, 127.3, 126.3, 121.5 (q, 1JC-F=255.6), 68.1 (q, 3JC-F=3.0). 19F NMR (282 MHz, CDCl$_3$): δ=−61.60 (s).

1-(Trifluoromethoxyacetyl)-2,3-dichlorobenzene

Yellow oil (at 25° C.). 1H NMR (300 MHz, CDCl$_3$): δ=7.57 (dd, J=8.1/1.8 Hz, 1H), 7.33 (dd, J=7.5/1.8 Hz, 1H), 7.26 (dd, J=8.1/7.5 Hz, 1H), 5.07 (s, 2H). 13C NMR (75 MHz, CDCl$_3$): δ=192.8, 137.1, 133.9, 133.2, 129.1, 127.7, 127.2, 121.1 (q, 1JC-F=255.2), 69.7 (q, 3JC-F=2.9). 19F NMR (282 MHz, CDCl$_3$): δ=−61.28 (s).

1-(Trifluoromethoxyacetyl)-3-chlorobenzene

Yellow oil (at 25° C.). 1H NMR (300 MHz, CDCl$_3$): δ=7.82 (dd, J=1.2/0.9 Hz, 1H), 7.73 (ddd, J=7.8/1.5/1.2 Hz, 1H), 7.54 (ddd, J=7.8/1.5/0.9 Hz, 1H), 7.40 (dd, J=7.8/7.8 Hz, 1H), 5.14 (s, 2H). 13C NMR (75 MHz, CDCl$_3$): δ=188.9, 135.2, 135.0, 134.0, 130.2, 127.8, 125.8, 121.4 (q, 1JC-F=255.1), 68.1 (q, 3JC-F=2.9). 19F NMR (282 MHz, CDCl$_3$): δ=−61.63 (s).

Enaminoketone Synthesis with DMF.DMA (Synthesis of Compounds of Formula I)

A solution of trifluoromethoxymethyl aryl ketone or trifluoromethoxymethyl heteroaryl ketone (1.0 eq.) and N,N-dimethylformamide dimethyl acetal (DMF.DMA) (10 eq.) was refluxed for 5 hours (monitored by TLC). The reaction mixture was cooled down, concentrated in vacuo and the residue was purified by chromatography over silica gel to yield pure desired trifluoromethoxylated enaminoketone.

(2Z or 2E)-3-(dimethylamino)-1-phenyl-2-(trifluoromethoxy)prop-2-en-1-one

Yellow oil. 1H NMR (300 MHz, CDCl$_3$): δ=7.60 (m, 2H); 7.47-7.33 (massif, 3H); 7.01 (broad s, 1H); 3.12 (s, 6H). 13C NMR (75 MHz, CDCl$_3$): δ=188.5; 145.4; 139.4; 130.6; 128.4; 128.2; 122.9 (m,); 121.3 (q, 1JC-F=255.0); 42.4 (broad s). 19F NMR (282 MHz, CDCl$_3$): δ=−58.96 (s).

(2Z or 2E)-3-(Dimethylamino)-1-(2-furyl)-2-(trifluoromethoxy)prop-2-en-1-one

Yellow oil (at 25° C.). 1H NMR (300 MHz, CDCl$_3$): δ=7.50 (dd, J=1.5/0.6 Hz, 1H), 7.46 (bs, 1H), 7.10 (dd, J=3.6/0.6 Hz, 1H), 6.61 (dd, J=3.6/1.5 Hz, 1H), 3.12 (s, 6H). 13C NMR (75 MHz, CDCl$_3$): δ=173.9, 151.6, 144.8, 143.5, 121.3, 121.1 (q, 1JC-F=255.0), 116.9, 111.5, 43.3, 42.6. 19F NMR (282 MHz, CDCl$_3$): δ=−59.47 (s).

(2Z or 2E)-3-(Dimethylamino)-1-(3',5'-dichlorophenyl)-2-(trifluoromethoxy)prop-2-en-1-one Yellow solid (at 25° C.). 1H NMR (300 MHz, CDCl$_3$): δ=7.41 (d, J=1.8 Hz, 2H), 7.36 (dd, J=1.8/1.8 Hz, 1H), 7.01 (bs, 1H), 3.10 (s, 6H). 13C NMR (75 MHz, CDCl$_3$): δ=184.7, 145.3, 141.8, 134.7, 130.1, 126.5, 121.7, 120.9 (q, 1JC-F=255.5), 30.7, 29.1. 19F NMR (282 MHz, CDCl$_3$): δ=−59.02 (s).

(2Z or 2E)-3-(Dimethylamino)-1-(2',3'-dichlorophenyl)-2-(trifluoromethoxy)prop-2-en-1-one Brown solid (at 25° C.). 1H NMR (300 MHz, CDCl$_3$): δ=7.47 (d, J=8.1 Hz, 1H), 7.26 (dd, J=8.1/7.5 Hz, 1H), 7.18 (d, J=7.5 Hz, 1H), 6.56 (bs, 1H), 3.13 (bs, 6H). 13C NMR (75 MHz, CDCl$_3$): δ=183.2, 147.0, 140.2, 132.9, 130.4, 128.7, 126.4, 125.7, 122.3, 120.6 (q, 1JC-F=255.4), 46.8, 37.8. 19F NMR (282 MHz, CDCl$_3$): δ=−58.74 (s).

(2Z or 2E)-3-(Dimethylamino)-1-(3'-chlorophenyl)-2-(trifluoromethoxy)prop-2-en-1-one Brown oil (at 25° C.). 1H NMR (300 MHz, CDCl$_3$): δ=7.52 (bs, 1H), 7.41 (ddd, J=7.5/1.8/1.2 Hz, 1H,), 7.35 (ddd, J=7.8/1.8/0.9 Hz, 1H), 7.27 (ddd, J=7.8/7.5/2.4 Hz, 1H), 6.96 (bs, 1H), 3.07 (s, 6H). 13C NMR (75 MHz, CDCl$_3$): δ=186.4, 145.3 (bs), 140.8, 134.0, 130.3, 129.3, 128.1, 126.2, 122.1 (bs), 121.0 (q, 1JC-F=255.1), 30.7. 19F NMR (282 MHz, CDCl$_3$): δ=−59.25 (s).

Preparation of Trifluoromethoxylated Pyrazoles (Synthesis of Compounds of Formula V-1 and V-2)

To a solution of trifluoromethoxylated enaminoketone (1.0 eq.) in glacial AcOH (C=0.2M) was added hydrazine hydrate (N$_2$H$_4$.H$_2$O) (1.0 eq.) and the resulting mixture was stirred at r.t. overnight. Then, an aqueous solution of AcONa (5%) was added and the mixture was extracted with DCM (3×). The organic layers were combined, washed with saturated aqueous NaHCO$_3$, brine, dried over MgSO$_4$, filtered and concentrated in vacuo. Purification by chromatography over silica gel finally afforded the pure trifluoromethoxylated pyrazole.

3-Phenyl-4-(trifluoromethoxy)-1H-pyrazole

White solid (at 25° C.); Mp=84-85° C.; 1H NMR (300 MHz, CDCl$_3$): δ=9.69 (bs, 1H), 7.73 (m, 2H), 7.62 (bs, 1H), 7.47-7.37 (massif, 3H); 13C NMR (75 MHz, CDCl$_3$): δ=138.4 (bs), 131.1 (bs), 129.1, 128.8, 129.6 (bs), 126.7, 120.8 (q, 1JC-F=256.6); 19F NMR (282 MHz, CDCl$_3$): δ=−60.77 (s).

3-(2-Furyl)-4-(trifluoromethoxy)-1H-pyrazole

Orange solid (at 25° C.). Mp=85° C. 1H NMR (300 MHz, CDCl$_3$): δ=11.45 (bs, 1H), 7.68 (d, J=1.2 Hz, 1H), 7.51 (dd, J=1.8/0.9 Hz, 1H), 6.80 (dd, J=3.3/0.9 Hz, 1H), 6.56 (dd, J=3.3/1.8 Hz, 1H). 13C NMR (75 MHz, CDCl$_3$): δ=144.1, 142.2, 132.2 (bs), 129.3 (bs), 124.9 (bs), 120.8 (q, 1JC-F=252.2), 111.8, 108.8. 19F NMR (282 MHz, CDCl$_3$): δ=−61.00 (s).

3-(3',5'-dichlorophenyl)-4-(trifluoromethoxy)-1H-pyrazole

White solid (at 25° C.). Mp=89° C. 1H NMR (300 MHz, CDCl$_3$): δ=11.56 (bs, 1H), 7.68 (bs, 1H), 7.61 (d, J=1.8 Hz, 2H), 7.36 (dd, J=1.8/1.8 Hz, 1H). 13C NMR (75 MHz, CDCl$_3$): δ=137.8 (bs), 135.6, 132.0, 131.9 (bs), 128.7, 125.0, 124.9 (bs), 120.5 (q, 1JC-F=257.6). 19F NMR (282 MHz, CDCl$_3$): δ=−60.92 (s).

3-(2',3'-dichlorophenyl)-4-(trifluoromethoxy)-1H-pyrazole

Yellow oil (at 25° C.). 1H NMR (300 MHz, CDCl$_3$): δ=11.13 (bs, 1H), 7.59 (bs, 1H), 7.51 (dd, J=7.5/1.8 Hz, 1H), 7.28 (dd, J=7.8/1.8 Hz, 1H), 7.22 (dd, J=7.8/7.5 Hz, 1H). 13C NMR (75 MHz, CDCl$_3$): δ=137.1 (bs), 133.9, 132.0, 131.3, 129.8 (bs), 129.7, 127.2, 125.0 (bs), 120.4 (q, 1JC-F=256.7). 19F NMR (282 MHz, CDCl$_3$): δ=−60.97 (s).

3-(3'-Chlorophenyl)-4-(trifluoromethoxy)-1H-pyrazole

Yellow solid (at 25° C.). Mp=44° C. 1H NMR (300 MHz, CDCl$_3$): δ=12.20 (bs, 1H), 7.63 (bs, 1H), 7.54 (bs, 1H), 7.51 (dd, J=7.8/1.8 Hz, 1H), 7.26 (dd, J=7.8/1.8 Hz, 1H), 7.24 (dd, J=7.8/7.8 Hz, 1H). 13C NMR (75 MHz, CDCl$_3$): δ=137.8, 134.8, 130.9 (bs), 130.5, 130.1, 128.9, 126.5, 125.7 (bs), 124.7, 120.6 (q, 1JC-F=257.0). 19F NMR (282 MHz, CDCl$_3$): δ=−61.10 (s).

Regioselective Preparation of Trifluoromethoxylated Methylpyrazoles (Synthesis of Compounds of Formula V-1)

To a solution of trifluoromethoxylated enaminoketone (1.0 eq.) in absolute EtOH (C=0.2M) was added methyl hydrazine (MeNHNH$_2$) (5.0 eq.) and the resulting mixture was stirred at r.t. for 5 hours (monitored by TLC). Then, the reaction mixture was concentrated in vacuo, the residue was dissolved in AcOEt, washed with water and brine, dried over Na$_2$SO$_4$, filtered and concentrated in vacuo. Purification by chromatography over silica gel finally afforded the pure trifluoromethoxylated methylpyrazole.

3-(2-Furyl)-1-methyl-4-(trifluoromethoxy)pyrazole

Colourless oil (at 25° C.). 1H NMR (300 MHz, CDCl$_3$): δ=7.48 (dd, J=1.8/0.9 Hz, 1H), 7.40 (d, J=0.9 Hz, 1H), 6.70 (dd, J=3.3/0.9 Hz, 1H), 6.47 (dd, J=3.3/1.8 Hz, 1H), 3.90 (s, 3H). 13C NMR (75 MHz, CDCl$_3$): δ=145.2, 142.2, 135.0, 129.1 (bs), 122.6, 120.6 (q, 1JC-F=256.0), 111.1, 108.1, 40.0. 19F NMR (282 MHz, CDCl$_3$): δ=−61.08 (s).

3-(3',5'-dichlorophenyl)-4-(trifluoromethoxy)-1-methylpyrazole

Yellow oil (at 25° C.). 1H NMR (300 MHz, CDCl$_3$): δ=7.72 (d, J=1.8 Hz, 2H), 7.43 (d, J=1.2 Hz, 1H), 7.30 (dd, J=1.8/1.8 Hz, 1H), 3.88 (s, 3H). 13C NMR (75 MHz, CDCl$_3$): δ=138.8, 135.1, 133.7, 130.7 (q, 3JC-F=2.4), 127.8, 124.6, 123.0, 120.5 (q, 1JC-F=257.0), 40.0. 19F NMR (282 MHz, CDCl$_3$): δ=−61.20 (s).

3-(2',3'-dichlorobenzyl)-4-(trifluoromethoxy)-1-methylpyrazole

White solid (at 25° C.). Mp=62° C. 1H NMR (300 MHz, CDCl$_3$): δ=7.51 (dd, J=7.8/1.5 Hz, 1H), 7.47 (bs, 1H), 7.33 (dd, J=7.8/1.8 Hz, 1H), 7.24 (dd, J=7.8/7.8 Hz, 1H), 3.93 (s, 1H). 13C NMR (75 MHz, CDCl$_3$): δ=140.8 (bs), 133.5, 132.3, 132.0, 131.1 (bs), 130.7, 130.0, 127.0, 122.1, 120.4 (q, 1JC-F=254.8), 40.0. 19F NMR (282 MHz, CDCl$_3$): δ=−61.12 (s).

3-(3'-Chlorophenyl)-4-(trifluoromethoxy)-1-methylpyrazole

Yellow oil (at 25° C.). 1H NMR (300 MHz, CDCl$_3$): δ=7.83 (bs, 1H), 7.69 (ddd, J=6.9/1.8/1.2 Hz, 1H), 7.36 (d, J=1.2 Hz, 1H), 7.29 (dd, J=7.5/6.9 Hz, 1H), 7.27 (dd, J=7.5/1.8 Hz, 1H), 3.80. 13C NMR (75 MHz, CDCl$_3$): δ=140.0, 134.4, 132.6, 130.5 (q, 3JC-F=2.4), 129.7, 127.9, 126.3, 124.4, 122.9 (bs), 120.5 (q, 1JC-F=256.4), 39.7. 19F NMR (282 MHz, CDCl$_3$): δ=−61.25 (s).

Oxidation of Heterocycles Bearing a 2-Furyl Moiety (Synthesis of Compounds of Formula VI)

To a solution of (2-furyl)-pyrazole (1.0 eq.) in a mixture of n-Hexane/AcOEt/H$_2$O (1:1:2, C=0.1M) was added NaIO$_4$ (10 eq.) (can be previously dissolved in H$_2$O before addition), followed by RuCl$_3$ (0.05M aqueous solution) (0.05 eq.). The heterogeneous reaction mixture was vigorously stirred at r.t. overnight. Then, the mixture was poured into solid NaCl (4 g/mmol of heterocycle) and a minimum of water. After 10 min of vigorous agitation, the reaction mixture was extracted with AcOEt (×3) (pH=3-4 for the combined aqueous layers). The organic layers were combined, dried over MgSO$_4$, filtered and concentrated in vacuo to give the crude desired carboxylic acid. The reaction may also be performed with (2-furyl)-pyridine or (2-furyl)-pyrimidine.

4-(Trifluoromethoxy)-3-carboxy-1H-pyrazole

White solid (at 25° C.). 1H NMR (300 MHz, (CD$_3$)$_2$CO): δ=10.66 (bs, 1H), 7.94 (d, J=0.9 Hz, 1H). 13C NMR (75 MHz, (CD$_3$)$_2$CO): δ=160.4, 134.6 (bs), 131.2, 128.0, 121.4 (q, 1JC-F=254.6). 19F NMR (282 MHz, (CD$_3$)$_2$CO): δ=−61.70 (s).

4-(Trifluoromethoxy)-3-carboxy-1-methylpyrazole

White solid (at 25° C.). 1H NMR (300 MHz, (CD$_3$)$_2$CO): δ=10.76 (bs, 1H), 7.98 (s, 1H), 3.98 (s, 3H). 13C NMR (75 MHz, (CD$_3$)$_2$CO): δ=161.3, 134.7, 134.1 (q, 3JC-F=2.7), 125.6, 121.3 (q, 1JC-F=254.5), 40.7. 19F NMR (282 MHz, (CD$_3$)$_2$CO): δ=−61.86 (s).

The invention claimed is:
1. Process for preparing an enaminoketone of formula I

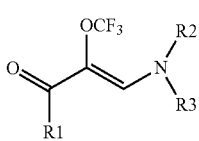

wherein
R$^1$ is C$_5$-C$_{10}$ aryl, optionally substituted by 1 to 5 halogen atoms, or C$_5$-C$_{10}$ aryl exhibiting one, two or more heteroatoms selected from oxygen and nitrogen, and
R$^2$ and R$^3$ are independently C$_1$-C$_6$ alkyl, C$_5$-C$_{10}$ aryl, C$_5$-C$_{10}$ aryl exhibiting one, two or more heteroatoms selected from oxygen and nitrogen, or form together a 5 or 7 membered ring
which comprises
(A) reacting a CF$_3$O-ketone of the formula II

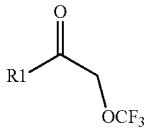

wherein R$^1$ is as defined above with an aminoformylation reagent.

2. Process according to claim 1, wherein
R$^1$ is 2-furyl, phenyl, or phenyl substituted with one or two chlorine atoms and
R$^2$ and R$^3$ are independently C$_1$-C$_6$ alkyl.

3. Process for preparing a trifluoromethoxypyrazold of formula V-1 or V-2

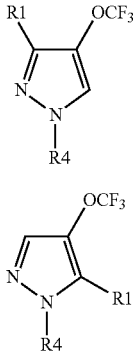

wherein
R$^1$ is C$_5$-C$_{10}$ aryl, optionally substituted by 1 to 5 halogen atoms, or C$_5$-C$_{10}$ aryl exhibiting one, two or more heteroatoms selected from oxygen and nitrogen,
and
R$^4$ is H, or C$_1$-C$_6$ Alkyl
which comprises
(A) reacting a CF$_3$O-ketone of the formula II

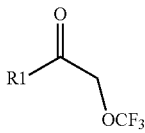

with an aminoformylation reagent to an enaminoketone of formula I

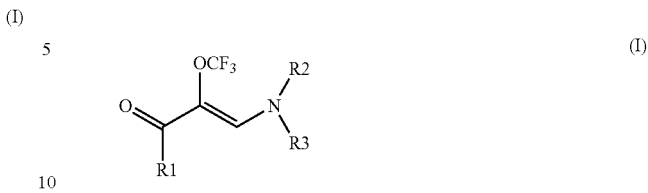

wherein R$^2$ and R$^3$ are independently C$_1$-C$_6$ alkyl, C$_5$-C$_{10}$ aryl, C$_5$-C$_{10}$ aryl exhibiting one, two or more heteroatoms selected from oxygen and nitrogen, or form together a 5 or 7 membered ring
and
(B) reacting the enaminoketone of formula (I) with an hydrazine of formula IV

R$^4$—NH—NH2 (IV)

wherein R$^4$ is as defined above.

4. Process for regioselectively preparing a trifluoromethoxypyrazoles of formula V-1

Wherein
R$^1$ is C$_5$-C$_{10}$ aryl, optionally substituted by 1 to 5 halogen atoms, or C$_5$-C$_{10}$ aryl exhibiting one, two or more heteroatoms selected from oxygen and nitrogen,
and
R$^4$ is H, or C$_1$-C$_6$ Alkyl
which comprises
(A) reacting a CF$_3$O-ketone of the formula II

with an aminoformylation reagent to an enaminoketone of formula I

wherein R$^2$ and R$^3$ are independently C$_1$-C$_6$ alkyl, C$_5$-C$_{10}$ aryl, C$_5$-C$_{10}$ aryl exhibiting one, two or more heteroatoms selected from oxygen and nitrogen, or form together a 5 or 7 membered ring and
and
(B) reacting the enaminoketone of formula (I) with an hydrazine of formula IV

R$^4$—NH—NH$_2$ (IV)

wherein (B) is performed in a solvent selected from the group consisting of methanol, ethanol, and trifluoroethanol.

5. Process according to claim 1, wherein the aminoformylation reagent used for (A) is selected from a compound of the formula III-1

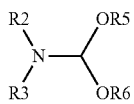
(III-1)

wherein $R^5$ and $R^6$ are $C_1$-$C_6$-Alkyl and a compound of the formula 111-2

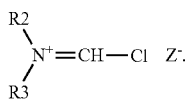
(III-2)

6. Process according to any of claim 1, wherein (A) is performed at a temperature of from 50° C. to 150° C.

7. Process according to claim 1, wherein the (A) is performed in a solvent selected from DMF, toluene, xylenes, chlorobenzenes, and dimethylacetamide.

8. Process according to claim 2, wherein (B) is performed at a temperature of from 0° C. to 50° C.

9. Process for preparing a trifluoromethoxypyrazolic acid of formula VI

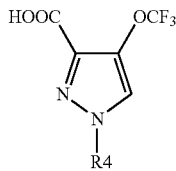
(VI)

Wherein $R^4$ is H, or $C_1$-$C_6$ Alkyl,
which comprises oxidizing a compound of formula V-1, wherein $R'$ is 2-Furyl.

10. Process according to claim 9, wherein the compound of formula V-1 is oxidized using an oxidant selected from $RuCl_3/NaIO_4$, $RuO_4$, $O_3$, $KMnO_4$, and $CrO_3$.

11. Process according to claim 9, wherein the process is performed in a solvent selected from hexane/AcOEt/$H_2O$, $CCl_4$/$CH_3CN$/$H_2O$, $H_2O$/MeCN/AcOEt, and $H_2O$/$CH_2Cl_2$/MeCN.

12. Compound of formula I

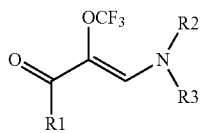
(I)

wherein
$R^1$ is $C_5$-$C_{10}$ aryl, optionally substituted by 1 to 5 halogen atoms, or $C_5$-$C_{10}$ aryl exhibiting one, two or more heteroatoms selected from oxygen and nitrogen, and $R^2$ and $R^3$ are independently $C_1$-$C_6$ alkyl, $C_5$-$C_{10}$ aryl, $C_5$-$C_{10}$ aryl exhibiting one, two or more heteroatoms selected from oxygen and nitrogen, or form together a 5 or 7 membered ring.

13. Compound of formula V-1 or V-2

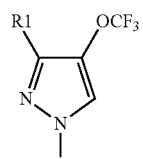
(V-1)

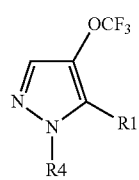
(V-2)

wherein $R^1$ is $C_5$-$C_{10}$ aryl, optionally substituted by 1 to 5 halogen atoms, or $C_5$-$C_{10}$ aryl exhibiting one, two or more heteroatoms selected from oxygen and nitrogen, and $R^4$ is H, or $C_1$-$C_6$ Alkyl.

14. Compound of formula V-1

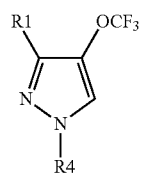
(V-1)

$R^1$ is $C_5$-$C_{10}$ aryl, optionally substituted by 1 to 5 halogen atoms, or $C_5$-$C_{10}$ aryl exhibiting one, two or more heteroatoms selected from oxygen and nitrogen, and $R^4$ is H, or $C_1$-$C_6$ Alkyl.

15. Compound of formula VI

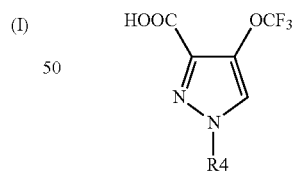
(VI)

wherein $R^4$ is H, or $C_1$-$C_6$ Alkyl.

* * * * *